United States Patent [19]

Guiliano et al.

[11] 4,282,359

[45] Aug. 4, 1981

[54] PURIFICATION OF CYANURIC ACID

[75] Inventors: Basil A. Guiliano, Plainsboro; Henry A. Pfeffer, Mercerville; Andrew D. Kurtz, Somerville, all of N.J.

[73] Assignee: FMC Corporation, Philadelphia, Pa.

[21] Appl. No.: 135,948

[22] Filed: Mar. 31, 1980

[51] Int. Cl.³ .......................................... C07D 251/32
[52] U.S. Cl. ................................................... 544/192
[58] Field of Search ........................................ 544/192

[56] References Cited

U.S. PATENT DOCUMENTS

| 2,943,088 | 6/1960 | Westfall | 260/248 |
|---|---|---|---|
| 3,065,233 | 11/1962 | Hopkins et al. | 260/248 |
| 3,117,968 | 1/1964 | Merkel et al. | 260/248 |
| 3,164,591 | 1/1965 | Walles et al. | 260/248 |
| 3,563,987 | 2/1971 | Berkowitz | 260/248 |
| 3,956,299 | 5/1976 | den Otter et al. | 260/248 |
| 3,994,892 | 11/1976 | den Otter et al. | 260/248 |
| 4,016,164 | 4/1977 | Berkowitz et al. | 260/248 |

FOREIGN PATENT DOCUMENTS 866459  10/1978  Belgium .

Primary Examiner—John M. Ford
Attorney, Agent, or Firm—John J. Jones; Frank Ianno

[57] ABSTRACT

Cyanuric acid is mechanically separated such as by filtration, centrifugation, or centrifugal filtration from a slurry of cyanuric acid, urea, biuret, and an inert solvent in which the urea is soluble at temperatures above about 170° C. to reduce the urea content of the recovered solid cyanuric acid. The biuret and solvent content of the solid cyanuric acid is also reduced.

14 Claims, No Drawings

PURIFICATION OF CYANURIC ACID

This invention relates to the production of cyanuric acid, and more particularly relates to the production of cyanuric acid in a solvent system and the subsequent separation of the cyanuric acid from the solvent slurry.

The main use for cyanuric acid is in the preparation of chloro substituted derivatives of isocyanuric acid such as sodium dichloroisocyanurate, potassium dichloroisocyanurate and trichloroisocyanuric acid. These derivative compounds have found extensive use in automatic dishwasher formulations, bleach formulations and in swimming pool disinfection.

Cyanuric acid is generally considered to exist in equilibrium as a keto-enol tautomer represented structurally as follows:

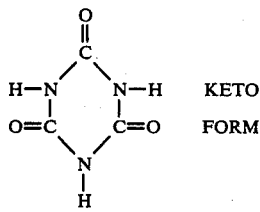
KETO FORM and

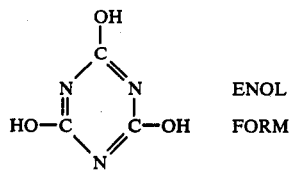
ENOL FORM

The preparation of cyanuric acid is well-known in the art. The basic commercial process involves the pyrolytic deamination of urea over several hours. The reaction can be expressed by the chemical equation:

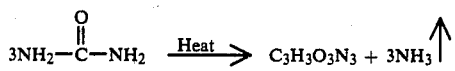

This reaction can be carried out in a dry system, that is, in the absence of a solvent, or it can be carried out in a solvent system wherein the urea is dissolved in a suitable solvent and the resulting solution is heated to effect the conversion of the urea to cyanuric acid. Many solvent systems have been disclosed in the patent literature. Basically, the solvent used must be capable of dissolving urea or biuret in substantial quantities, and the cyanuric acid must be relatively insoluble therein. Additionally, the solvent must not react with urea, biuret or cyanuric acid. Examples of suitable solvents are the alkyl sulfones disclosed in U.S. Pat. No. 3,065,233, issued to Hopkins et al; and the solvents of the general formula

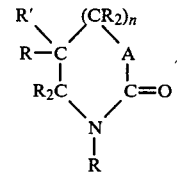

wherein R is hydrogen or a lower alkyl group containing 1-4 carbon atoms, R' is hydrogen, a lower alkyl group containing 1-4 carbon atoms, or phenyl, A is an oxygen atom or $CR_2$, R being as defined above, and n is zero or one when A is oxygen and n is zero when A is $CR_2$, as disclosed in U.S. Pat. No. 3,164,591, issued to Walles, et al. The compounds of Walles, et al would include 5-methyl-2-oxazolidinone, 5-phenyl-2-oxazolidinone, 2-pyrrolidone, and many others.

Following the production of cyanuric acid in a solvent system, the reaction mixture would contain solid cyanuric acid, the solvent, some dissolved cyanuric acid depending upon the solvent and its temperature, biuret, and unreacted urea, from which the solid cyanuric acid must be separated.

In conducting the separation of the cyanuric acid from the slurry, it is necessary for many applications to produce a cyanuric acid product that is substantially pure and free of the urea, biuret and solvent. Walles, et al, in U.S. Pat. No. 3,164,591, separates the solid cyanuric acid from the solvent slurry by filtering at room temperature so as to maximize the amount of cyanuric acid which would precipitate from the reaction mixture and therefore be readily recoverable. In so operating, however, the separated solid cyanuric acid contains substantial amounts of urea, biuret and the solvent, thereby requiring additional process steps to effect further purification. In U.S. Pat. No. 3,956,299, den Otter, et al, teach that a hot filtration at 150° C. reduces the amounts of urea and biuret retained by the solid cyanuric acid. Even after filtering at 150° C., however, the urea content of the solid cyanuric acid is quite high, thereby requiring further processing.

It has now been discovered that solid cyanuric acid can be recovered in a more purified state from a slurry of solid, cyanuric acid in an inert solvent containing dissolved urea and/or biuret by mechanically separating the solid cyanuric acid from the slurry while maintaining a temperature of greater than about 170° C. Operating at such a temperature unexpectedly results in a significant reduction in the amount of urea retained by the solid cyanuric acid as compared to separations conducted below this temperature. Further, the amount of solvent retained on the solid cyanuric acid is also reduced as compared to lower temperature separations.

In carrying out the present invention, solid cyanuric acid is mechanically separated from a slurry of cyanuric acid in a solvent in which urea and/or biuret is dissolved, while maintaining the temperature of these materials above 170° C. The mechanical separation of the solid cyanuric acid can be, for example, by filtration, centrifugation or by centrifugal filtration. The term mechanical separation, as used herein, is intended to distinguish from those separation techniques relying upon the distillation, evaporation, or drying of the slurry whereby the separation takes place principally by changing the physical state of the urea and the solvent.

The concentration of urea retained by the solid cyanuric acid decreases somewhat as the mechanical separation temperature increases from room temperature. Hence, at a 150° C. mechanical separation temperature, the concentration of urea retained by the solid cyanuric acid is less than the concentration of urea retained following a mechanical separation of 100° C. The difference in these concentrations is however, relatively insignificant. Above about 170° C., however, a dramatic and substantial decrease in the urea concentration is achieved, such that for example, the urea concentration in the solid cyanuric acid following mechanical separation at 180° C. exhibits a five-fold and sometimes a ten-fold and greater decrease as compared to the same separation conducted at 170° C. Preferably, the mechanical separation should be conducted at temperatures above about 180° C. and more preferably above about 200° C. to further decrease the urea concentration in the cyanuric acid.

By operating the mechanical separation at temperatures above about 170° C., a further advantage is achieved in that the concentrations of biuret and solvent retained by the solid cyanuric acid are also decreased as compared to the lower separation temperatures of the prior art. The biuret would be present from a partial conversion of the urea during the reaction step.

Where it is desired to produce a pure solid cyanuric acid from a mixture of cyanuric acid and urea, the mixture can be slurried in a suitable solvent, which is either pre-heated to above about 170° C. or subsequent to slurrying is heated to a temperature above about 170° C., and subjected to a mechanical separation to recover the solid cyanuric acid. Hence in those cases where an insufficient separation of cyanuric acid from urea has been conducted by means outside the present invention, the advantages of the present invention can still be achieved by slurrying the cyanuric acid and urea in a suitable solvent and proceeding according to the invention herein.

Any of the solvents having the properties as discussed above are suitable for use in carrying out this invention. Sulfolane is the preferred solvent.

As used herein, any mixture of urea and cyanuric acid encompasses within its meaning urea cyanurate, which is generally considered to be a weakly formed complex of urea and cyanuric acid.

The following examples are presented to illustrate the invention and are not deemed to be limiting thereof. All percentages are by weight unless otherwise indicated.

EXAMPLE 1

Following the production of cyanuric acid in a sulfolane solvent system, a reactor sample containing approximately 30% cyanuric acid, 5% urea, 2% biuret and 63% sulfolane was filtered on a buchner funnel at various temperatures and residence times. The results of the six runs so conducted are shown in Table 1. The grams of urea per gram of cyanuric acid in the filter cake decreased dramatically at above 170° C., for example, at 180° C., for all residence times as compared at the concentration changes in operating below 170° C., for example at 160° C. At 160° C., there is 0.082 grams of urea per gram of cyanuric acid in the filter cake for a residence time of 60 minutes. At 170° C. and a residence time of 60 minutes, there is 0.05 grams of urea per gram of cyanuric acid in the filter cake, which is only a 1.6 fold decrease over 160° C. At 180° C. and a residence time of 60 minutes, there is 0.005 grams of urea per gram of cyanuric acid in the filter cake, which is a 10 fold decrease over 170° C.

EXAMPLE 2

A mixture containing 29.2% cyanuric acid, 4.4% urea, and 66.4% sulfolane was filtered on a buchner funnel at various temperatures and residence times. The results of the three runs so conducted are shown in Table 2. The grams of urea per gram of cyanuric acid in the filter cake decreased dramatically in going from 150° C. to 200° C. for all residence times (about 24 fold on the average) as compared to the decrease achieved in going from 100° C. to 150° C. (about 1.5 fold on the average).

EXAMPLE 3

Following the production of cyanuric acid in a sulfolane solvent system, a reaction sample containing approximately 23.7% cyanuric acid, 2.3% urea, 1.4% biuret, and 72.7% sulfolane was centrifuged at temperatures of 80° C. and 200° C. using a solid bowl centrifuge. The results of the two runs so conducted are shown in Table 3. Almost a 50 fold decrease in the urea content was achieved in going from 80° C. to 200° C.

TABLE 1

Filtration of Cyanuric Acid, Urea, Biuret and Sulfolane Mixtures

| Run No. | Filtration Temp. (°C.) | Residence Time (min) | Filter Cake Analyses | | |
|---|---|---|---|---|---|
| | | | Urea[1] | Biuret[2] | Sulfolane[3] |
| 1 | 100 | 10 | 0.14 | 0.05 | 0.29 |
| | 100 | 30 | 0.14 | 0.05 | 0.32 |
| | 100 | 60 | 0.15 | 0.05 | 0.32 |
| | 100 | 120 | 0.14 | 0.05 | 0.31 |
| 2 | 150 | 10 | 0.10 | 0.009 | 0.21 |
| | 150 | 30 | 0.10 | 0.008 | 0.19 |
| | 150 | 60 | 0.10 | 0.008 | 0.21 |
| | 150 | 120 | 0.11 | 0.008 | 0.20 |
| 3 | 160 | 5 | 0.081 | 0.009 | 0.22 |
| | 160 | 10 | 0.081 | 0.009 | 0.20 |
| | 160 | 30 | 0.070 | 0.007 | 0.16 |
| | 160 | 60 | 0.002 | 0.008 | 0.18 |
| 4 | 170 | 5 | 0.05 | 0.011 | 0.25 |
| | 170 | 10 | 0.06 | 0.008 | 0.20 |
| | 170 | 30 | 0.05 | 0.008 | 0.20 |
| | 170 | 60 | 0.05 | 0.008 | 0.21 |
| 5 | 180 | 5 | 0.012 | 0.006 | 0.16 |
| | 180 | 10 | 0.010 | 0.006 | 0.14 |
| | 180 | 30 | 0.008 | 0.006 | 0.13 |
| | 180 | 60 | 0.005 | 0.006 | 0.14 |
| 6 | 200 | 30 | 0.008 | 0.005 | 0.15 |
| | 200 | 60 | 0.005 | 0.004 | 0.13 |

[1] g urea/g cyanuric acid
[2] g biuret/g cyanuric acid
[3] g sulfolane/g cyanuric acid

TABLE 2

Filtration of Cyanuric Acid, Urea and Sulfolane Mixtures

| Run No. | Filtration Temp. (°C.) | Residence Time (min) | Filter Cake Analyses | |
|---|---|---|---|---|
| | | | Urea[1] | Sulfolane[2] |
| 7 | 100 | 5 | 0.14 | 0.40 |
| | 100 | 10 | 0.15 | 0.42 |
| | 100 | 30 | 0.14 | 0.37 |
| | 100 | 60 | 0.14 | 0.40 |
| 8 | 150 | 5 | 0.11 | 0.28 |
| | 150 | 10 | 0.10 | 0.28 |
| | 150 | 30 | 0.11 | 0.23 |
| | 150 | 60 | 0.09 | 0.26 |
| 9 | 200 | 5 | 0.006 | 0.18 |
| | 200 | 10 | 0.007 | 0.21 |
| | 200 | 30 | 0.006 | 0.22 |

TABLE 2-continued

Filtration of Cyanuric Acid, Urea and Sulfolane Mixtures

| Run No. | Filtration Temp. (°C.) | Residence Time (min) | Filter Cake Analyses | |
|---|---|---|---|---|
| | | | Urea[1] | Sulfolane[2] |
| | 200 | 60 | 0.002 | 0.18 |

[1] g urea/g cyanuric acid
[2] g sulfolane/g cyanuric acid

TABLE 3

Centrifugation of Cyanuric Acid, Urea, Biuret and Sulfolane Mixtures

| Run No. | Centrifuge Temp. (°C.) | Centrifugation Cake Analyses | | |
|---|---|---|---|---|
| | | Urea[1] | Biuret[2] | Sulfolane[3] |
| 10 | 80 | 0.09 | 0.043 | 0.303 |
| 11 | 200 | 0.002 | 0.006 | 0.023 |

[1] g urea/g cyanuric acid
[2] g biuret/g cyanuric acid
[3] g sulfolane/g cyanuric acid

We claim:

1. A process for recovering solid cyanuric acid in a more purified state from a slurry of solid cyanuric acid in an inert solvent containing dissolved urea and/or biuret and in which solvent the cyanuric acid is insoluble, which comprises mechanically separating the solid cyanuric acid from the slurry while maintaining the slurry at a temperature greater than about 170° C.

2. A process for recovering solid cyanuric acid in a more purified state from a mixture of urea and cyanuric acid, which comprises slurrying the mixture in an inert solvent in which the cyanuric acid is insoluble and the urea is soluble and is dissolved, heating the slurry to a temperature greater than about 170° C., and mechanically separating solid cyanuric acid from the slurry while maintaining the slurry at a temperature greater than about 170° C.

3. A process for recovering solid cyanuric acid in a more purified state from a mixture of urea and cyanuric acid, which comprises forming at a temperature greater than about 170° C. a slurry of solid cyanuric acid in an inert solvent in which the cyanuric acid is insoluble and the urea is soluble and is dissolved, and mechanically separating solid cyanuric acid from the slurry while maintaining the slurry at a temperature greater than about 170° C.

4. In a process for preparing cyanuric acid by heating a compound selected from the group consisting of urea, biuret and mixtures thereof in an inert solvent to form a slurry containing solid cyanuric acid, and recovering the solid cyanuric acid from the slurry by mechanical separation, the improvement which comprises mechanically separating the solid cyanuric acid from the slurry while maintaining a temperature of greater than about 170° C. whereby the solid cyanuric acid is recovered in a more purified state.

5. The process of claims 1, 2, 3 or 4 wherein the inert solvent is selected from the group consisting of dimethylsulfone, dipropylsulfone, o-chlorocresol, p-chlorocresol, N-methylpyrrolidone, N-cyclohexylpyrrolidone, 5-methyl-2-oxazolidinone, 2-methylcyclohexanol, 2,6-dimethylcyclohexanol, 2,4,6-trimethylcyclohexanol, sulfolane and methyl substituted derivatives of sulfolane.

6. The process of claims 1, 2, 3 or 4 wherein the temperature is at least about 180° C.

7. The process of claims 1, 2, 3 or 4 wherein the step of mechanically separating the solid cyanuric acid from the slurry is achieved by filtration.

8. The process of claims 1, 2, 3 or 4 wherein the step of mechanically separating the solid cyanuric acid from the slurry is achieved by centrifugation.

9. The process of claims 1, 2, 3 or 4 wherein the step of mechanically separating the solid cyanuric acid from the slurry is achieved by centrifugal filtration.

10. In a process for preparing cyanuric acid by heating a compound selected from the group consisting of urea, biuret and mixtures thereof in sulfolane to form a slurry containing solid cyanuric acid, and recovering the solid cyanuric acid from the slurry by filtration, the improvement which comprises filtering the slurry at a temperature of at least about 180° C. whereby the solid cyanuric acid is recovered in a more purified state.

11. In a process for preparing cyanuric acid by heating a compound selected from the group consisting of urea, biuret and mixtures thereof in sulfolane to form a slurry containing solid cyanuric acid, and recovering the solid cyanuric acid from the slurry by centrifugation, the improvement which comprises centrifuging the slurry at a temperature of at least about 180° C. whereby the solid cyanuric acid is recovered in a more purified state.

12. In a process for preparing cyanuric acid by heating a compound selected from the group consisting of urea, biuret and mixtures thereof in sulfolane to form a slurry containing solid cyanuric acid, and recovering the solid cyanuric acid from the slurry by centrifugal filtration, the improvement which comprises centrifugally filtering the slurry at a temperature of at least about 180° C. whereby the solid cyanuric acid is recovered in a more purified state.

13. The process of claims 1, 2, 3, 4, 10, 11 or 12 wherein the temperature is at least about 200° C.

14. The process of claims 1, 2, 3, 4, 10, 11 or 12 wherein the solid cyanuric acid recovered in a more purified state contains no more than about 0.01 grams of urea per gram of cyanuric acid.

* * * * *